(12) United States Patent
Larsen et al.

(10) Patent No.: US 11,096,696 B2
(45) Date of Patent: Aug. 24, 2021

(54) OCCLUSIVE MEDICAL DEVICE

(71) Applicant: BOSTON SCIENTIFIC SCIMED, INC., Maple Grove, MN (US)

(72) Inventors: Steven R. Larsen, Lino Lakes, MN (US); Daniel H. VanCamp, Elk River, MN (US); David John Onushko, Minneapolis, MN (US); Lindsay Marie Godin, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 110 days.

(21) Appl. No.: 16/245,279

(22) Filed: Jan. 11, 2019

(65) Prior Publication Data

US 2019/0216468 A1 Jul. 18, 2019

Related U.S. Application Data

(60) Provisional application No. 62/616,515, filed on Jan. 12, 2018.

(51) Int. Cl.
*A61B 17/12* (2006.01)
*A61B 17/00* (2006.01)

(52) U.S. Cl.
CPC .... *A61B 17/12122* (2013.01); *A61B 17/0057* (2013.01); *A61B 17/12031* (2013.01); *A61B 17/12113* (2013.01); *A61B 17/12168* (2013.01); *A61B 17/12172* (2013.01); *A61B 17/1219* (2013.01); *A61B 17/12027* (2013.01); *A61B 17/12177* (2013.01); *A61B 2017/00632* (2013.01); *A61B 2017/00862* (2013.01); *A61B 2017/00867* (2013.01); *A61B 2017/1205* (2013.01)

(58) Field of Classification Search
CPC .......... A61B 17/12122; A61B 17/0057; A61B 17/12031; A61B 17/12113; A61B 17/12168; A61B 17/12172; A61B 17/1219; A61B 2017/1205; A61B 17/1215; A61B 17/1214; A61B 17/12177
See application file for complete search history.

(56) References Cited

U.S. PATENT DOCUMENTS

2002/0111647 A1* 8/2002 Khairkhahan ........ A61M 25/10
606/200
2005/0177182 A1* 8/2005 van der Burg ............ A61F 2/01
606/157

(Continued)

FOREIGN PATENT DOCUMENTS

WO 03063732 A2 8/2003

OTHER PUBLICATIONS

International Search Report and Written Opinion dated Apr. 18, 2019 for International Application No. PCT/US2019/013121.

*Primary Examiner* — Katrina M Stransky
(74) *Attorney, Agent, or Firm* — Seager, Tufte & Wickhem LLP

(57) ABSTRACT

An example occlusive implant is disclosed. The example occlusive implant includes an expandable framework configured to shift between a collapsed configuration and an expanded configuration, an occlusive member disposed along at least a portion of the expandable framework and a sealing member disposed along the occlusive member, wherein the occlusive member includes at least a first cellular tissue growth pathway.

12 Claims, 11 Drawing Sheets

(56) References Cited

U.S. PATENT DOCUMENTS

| | | |
|---|---|---|
| 2014/0074151 A1 | 3/2014 | Tischler et al. |
| 2014/0188157 A1 | 7/2014 | Clark et al. |
| 2015/0133989 A1 | 5/2015 | Lubock et al. |
| 2017/0135801 A1* | 5/2017 | Delaney, Jr. ............... A61F 2/01 |
| 2017/0303932 A1 | 10/2017 | Clark et al. |

* cited by examiner

OCCLUSIVE MEDICAL DEVICE

CROSS-REFERENCE TO RELATED APPLICATIONS

This application claims the benefit of priority under 35 U.S.C. § 119 to U.S. Provisional Application Ser. No. 62/616,515, filed Jan. 12, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

An example occlusive implant includes an expandable framework configured to shift between a collapsed configuration and an expanded configuration, an occlusive member disposed along at least a portion of the expandable framework and a sealing member disposed along the occlusive member, wherein the occlusive member includes at least a first cellular tissue growth pathway.

In addition or alternatively, wherein the occlusive member includes a plurality of filaments which form the first cellular growth pathway.

In addition or alternatively, wherein the plurality of filaments are woven together.

In addition or alternatively, wherein the occlusive member includes a monolithic sheet of material.

In addition or alternatively, wherein the sheet of material has one or more apertures therein, and wherein the pathway is formed from material extending between the one or more apertures.

In addition or alternatively, wherein the pathway extends radially away from a central region of the occlusive member.

In addition or alternatively wherein the central region of the occlusive member includes a termination member.

In addition or alternatively, wherein at least one of the filaments forming the first cellular growth pathway is coupled to the termination member.

In addition or alternatively, wherein the first cellular growth pathway is continuous between the termination member an outer edge region of the implant.

In addition or alternatively, wherein at least one of the plurality of filaments includes a longitudinally extending channel, and wherein the channel is configured to promote cellular tissue growth along its length thereof.

In addition or alternatively, wherein the at least two of the plurality of filaments are coupled together via at least one lateral member.

In addition or alternatively, wherein the occlusive implant further comprising a second tissue growth pathway positioned adjacent to the first tissue growth pathway.

Another example medical implant for occluding a left atrial appendage includes:
an expandable framework configured to shift between a collapsed configuration and an expanded configuration; and
an occlusive member disposed along at least a portion of the expandable framework, the occlusive member including central region;
wherein the occlusive member includes a plurality of cellular growth pathways extending radially away from the central region;
wherein each of the cellular growth pathways is configured to promote continuous cellular tissue growth along its length thereof.

In addition or alternatively, wherein the occlusive member includes a plurality of filaments which form the plurality of cellular growth pathways.

In addition or alternatively, wherein the plurality of filaments are woven together.

In addition or alternatively, wherein the occlusive member includes a monolithic sheet of material.

In addition or alternatively, wherein the sheet of material has one or more apertures therein, and wherein the plurality of cellular growth pathways are formed from material extending between the one or more apertures.

In addition or alternatively, wherein at least one of the plurality of filaments includes a longitudinally extending channel, and wherein the channel is configured to promote cellular tissue growth along its length thereof.

In addition or alternatively, wherein the at least two of the plurality of filaments are coupled together via at least one lateral member.

An example method for occluding a left atrial appendage includes:
advancing an occlusive implant to the left atrial appendage, the occlusive implant including:
an expandable framework; and
an occlusive member disposed along at least a portion of the expandable framework, wherein the occlusive member includes a central region;
wherein the occlusive member includes at least a first cellular tissue growth pathway extending radially away from the central region; and
expanding the expandable framework within the left atrial appendage.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
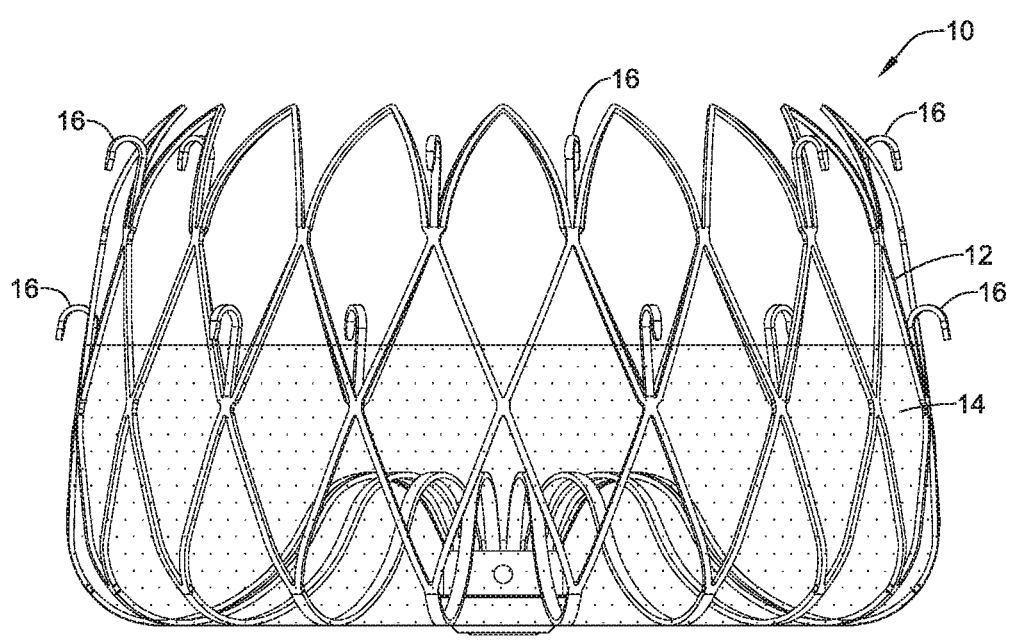
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thrombolytic material entering the blood stream from the left atrial appendage. Example medical devices and/or occlusive implants which promote endothelial tissue growth to seal the left atrial appendage (or other similar openings) are disclosed herein.

FIG. 1 illustrates an example occlusive implant 10. The implant 10 may include an expandable framework 12. The occlusive implant 10 may also include an occlusive member 14 disposed on, disposed over, disposed about, or covering at least a portion of the expandable framework 12. In some embodiments, the occlusive member 14 may be disposed on, disposed over, disposed about or cover at least a portion of an outer (or outwardly-facing) surface of the expandable framework 12. FIG. 1 further illustrates that the occlusive member 14 may extend only partially along the longitudinal extent of the expandable framework 12. However, this is not intended to be limiting. Rather, the occlusive member 14 may extend along the longitudinal extent of the expandable framework to any degree (e.g., the full longitudinal extend of the expandable framework 12).

In some embodiments, the occlusive member 14 may be permeable or impermeable to blood and/or other fluids, such as water. In some embodiments, the occlusive member 14 may include a woven, braided and/or knitted material, a fiber, a sheet-like material, a fabric, a polymeric membrane, a metallic or polymeric mesh, a porous filter-like material, or other suitable construction. In some embodiments, the occlusive member 14 may prevent thrombi (i.e. blood clots, etc.) from passing through the occlusive member 14 and out of the left atrial appendage into the blood stream. In some embodiments, the occlusive member 14 may promote endothelialization after implantation, thereby effectively removing the left atrial appendage from the patient's circulatory system. Some suitable, but non-limiting, examples of materials for the occlusive member 14 are discussed below.

FIG. 1 further illustrates that the expandable framework 12 may include a plurality of anchor members 16 disposed about a periphery of the expandable framework 12. The plurality of anchor members 16 may extend radially outward from the expandable framework 12. In some embodiments, at least some of the plurality of anchor members 16 may each have and/or include a body portion and a tip portion projecting circumferentially therefrom, as shown in FIG. 1. Some suitable, but non-limiting, examples of materials for the expandable framework 12 and/or the plurality of anchor members 16 are discussed below.

In some examples, the expandable framework 12 and the plurality of anchor members 16 may be integrally formed and/or cut from a unitary member. In some embodiments, the expandable framework 12 and the plurality of anchor members 16 may be integrally formed and/or cut from a unitary tubular member and subsequently formed and/or heat set to a desired shape in the expanded configuration. In some embodiments, the expandable framework 12 and the plurality of anchor members 16 may be integrally formed and/or cut from a unitary flat member, and then rolled or formed into a tubular structure and subsequently formed and/or heat set to the desired shape in the expanded configuration. Some exemplary means and/or methods of making and/or forming the expandable framework 12 include laser cutting, machining, punching, stamping, electro discharge machining (EDM), chemical dissolution, etc. Other means and/or methods are also contemplated.

As illustrated in FIG. 1, the plurality of anchor members 16 disposed along the expandable framework 12 may include two rows of anchor members 16. However, this is not intended to be limiting. Rather, the expandable framework 12 may include a single row of anchor members 16. In other examples, the expandable framework 12 may include more than two rows of anchor members 16. For example, in some instances the expandable framework 12 may include 1, 2, 3, 4 or more rows of anchor members 16.

Figure 2:
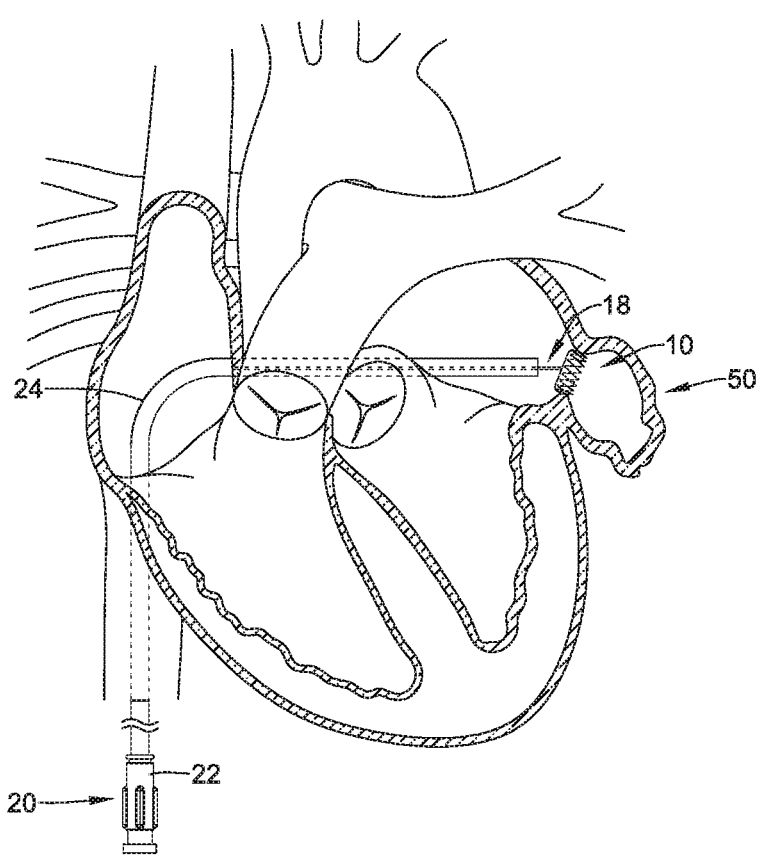
FIG. 2 illustrates an example occlusive implant positioned in the heart.

FIG. 2 illustrates that the occlusive implant 10 may be inserted and advanced through a body lumen via an occlusive implant delivery system 20. FIG. 2 further illustrates the occlusive implant 10 being delivered and positioned within the left atrial appendage 50. In some instances, an occlusive implant delivery system 20 may include a delivery catheter 24 which is guided toward the left atrium via various chambers and lumens of the heart (e.g., the inferior vena cava, the right atrium, etc.) to a position adjacent the left atrial appendage 50.

The delivery system 20 may include a hub member 22 coupled to a proximal region of the delivery catheter 24. The hub member 22 may be manipulated by a clinician to direct the distal end region of the delivery catheter 24 to a position adjacent the left atrial appendage 50. In some embodiments, an occlusive implant delivery system may include a core wire 18. Further, a proximal end of the expandable framework 12 may be configured to releasably attach, join, couple, engage, or otherwise connect to the distal end of the core wire 18. In some embodiments, an end region of the expandable framework 12 may include a threaded insert coupled thereto. In some embodiments, the threaded insert may be configured to and/or adapted to couple with, join to, mate with, or otherwise engage a threaded member disposed at the distal end of a core wire 18. Other means of releasably coupling and/or engaging the proximal end of the expandable framework 12 to the distal end of the core wire 18 are also contemplated.

Figure 3:
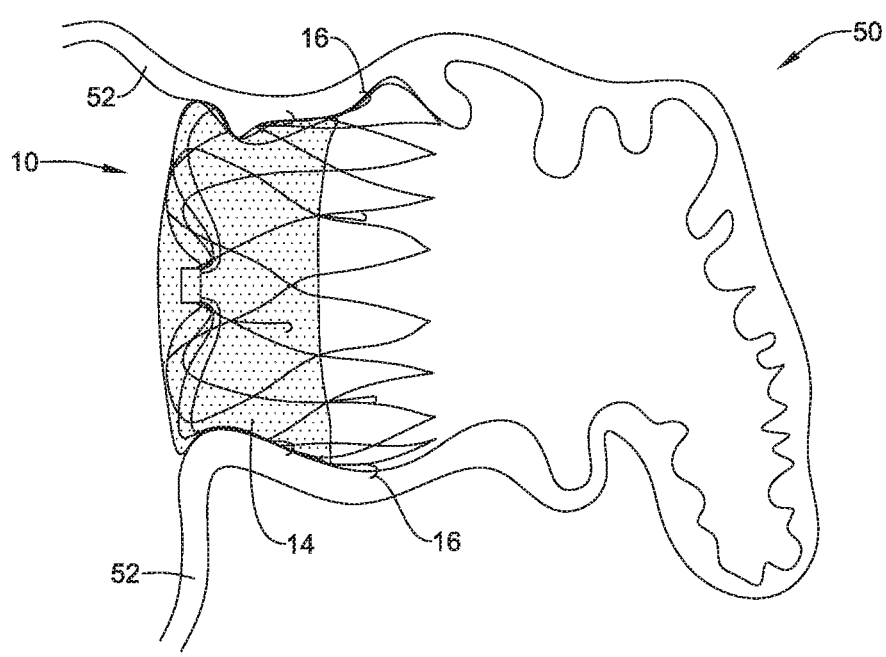
FIG. 3 illustrates an example occlusive implant positioned in the left atrial appendage.

FIG. 3 illustrates the occlusive implant 10 positioned within the left atrial appendage 50 via the delivery catheter 24 (described above with respect to FIG. 2). As discussed above, in some examples, the implant 10 may be configured to shift between a collapsed configuration and an expanded configuration. For example, in some instances, the occlusive implant 10 may be in a collapsed configuration during delivery via an occlusion implant delivery system, whereby the occlusive implant 10 expands to an expanded configuration once deployed from the occlusion implant delivery system.

Additionally, FIG. 3 illustrates that the expandable framework 12 may be compliant and, therefore, substantially conform to and/or be in sealing engagement with the shape and/or geometry of a lateral wall of a left atrial appendage 50 in the expanded configuration. In some embodiments, the occlusive implant 10 may expand to a size, extent, or shape less than or different from a maximum unconstrained extent, as determined by the surrounding tissue 52 and/or lateral wall of the left atrial appendage. Additionally, FIG. 3 illustrates that the expandable framework 12 may be held fixed adjacent to the left atrial appendage by one or more anchoring members 16.

Further, it can be appreciated that the elements of the expandable framework 12 may be tailored to increase the flexibility and compliance of the expandable framework 12 and/or the occlusive implant 10, thereby permitting the expandable framework 12 and/or the occlusive implant 10 to conform to the tissue around it, rather than forcing the tissue to conform to the expandable framework 12 and/or the occlusive implant 10. Additionally, in some instances, it may be desirable to design the occlusive implant 10 discussed above to include various features, components and/or configurations which improve the sealing capabilities of the occlusive implant 10 within the left atrial appendage. Several example occlusion devices including various sealing features are disclosed below.

Figure 4:
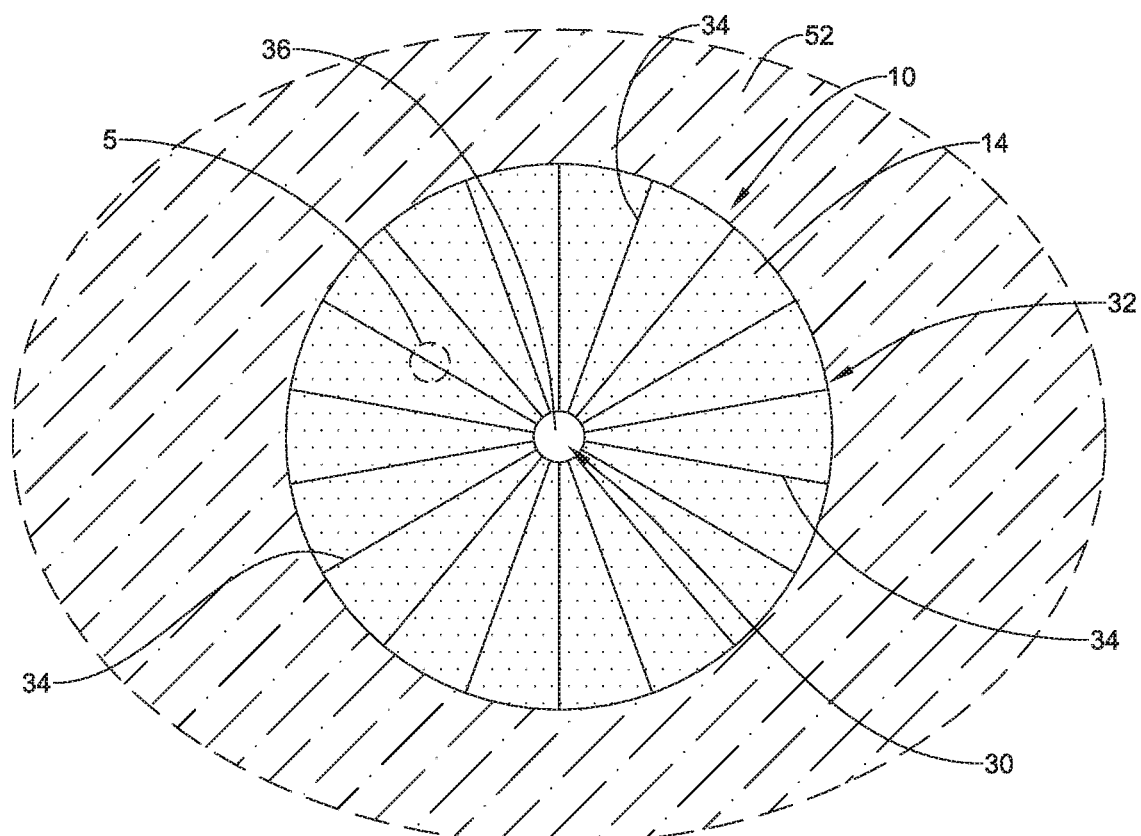
FIG. 4 illustrates an end view of an example occlusive implant positioned in the left atrial appendage.

FIG. 4 illustrates the example occlusive implant 10 positioned within the left atrial appendage 50 (described above). The positioning of the occlusive implant 10 shown in FIG. 4 is similar to that shown in FIG. 3, however, FIG. 4 illustrates an alternate view of the occlusive implant 10. In particular, FIG. 4 illustrates an end view of the occlusive implant 10 positioned in the left atrial appendage (e.g., a view of the bottom of the occlusive device 10 looking inward at the left atrial appendage). It can be appreciated that the occlusive device 10 may be able to conform to the specific shape and/or geometry of a lateral wall of a left atrial appendage 50. In other words, the occlusive device 10 may fill and/or conform to the specific shape and/or geometry of a lateral wall of a left atrial appendage 50 when positioned adjacent thereto.

As shown in FIG. 4, the occlusive member 14 may extend from a central region 30 radially outward along the framework 12. It can be appreciated from both FIG. 3 and FIG. 4 that the occlusive member 14 may extend around the bottom portion of the framework 12 and up along a portion of the sides of the framework 12. In particular, FIG. 4 illustrates the occlusive member 14 spanning the bottom portion of the framework 12. Further, FIG. 4 illustrates that the occlusive member 14 may extend from a central region 30 to a position where it contacts tissue 52 which is surrounding the left atrial appendage 50. It can be appreciated from FIG. 4 that the occlusive member 14 may extend circumferentially around the entire opening of the left atrial appendage 50. In other words, a portion of the occlusive member 14 may be positioned adjacent to the tissue 52 which is adjacent to the left atrial appendage (e.g., positioned around the circumference of the opening to the left atrial appendage 50).

As discussed above, in some instances it may be desirable to seal the left atrial appendage from the left atrium. Accordingly, in some instances it may be desirable to promote endothelial tissue growth across the occlusive member 14. The endothelial tissue may grow across the entire surface of the occlusive member 14, thereby providing a complete seal of the left atrial appendage 50 from the left atrium. Therefore, it can be appreciated that it may be desirable to promote endothelial tissue to grow quickly. Accordingly, in some instances it may be desirable to design the occlusive member 14 to limit obstacles for endothelial tissue growth. In other words, in some instances it may be desirable to design the occlusive member 14 to include features which maximize the efficiency in which the endothelial tissue migrates (e.g., replicates and advances) across the occlusive member 14.

As described above, FIG. 4 illustrates the occlusive member 14 spanning across the bottom portion of the framework 12. However, FIG. 4 further illustrates that the occlusive member includes a plurality of preferred growth pathways 34 (depicted as the solid lines) extending radially outward from the central region 30. While not shown in FIG. 4, it can be appreciated that the preferred growth pathways 34 may extend radially outward from the central region 30 and wrap up along the sides of the occlusive member 14. However, in other examples, the preferred growth pathways 34 may extend along the bottom portion of the framework 12 (as shown in FIG. 4) and terminate at a position adjacent to the tissue 52 surrounding the left atrial appendage. It is noted that the tissue 52 may include endothelial tissue.

FIG. 4 further illustrates that the preferred growth pathways 34 may be constructed such that they promote endothelial tissue to grow radially inward from an outer edge region 32. The outer edge region 32 may be defined as the region in which the occlusive member 14 meets (e.g., contacts, abuts, presses against, etc.) the surrounding tissue 52 adjacent the left atrial appendage. FIG. 4 illustrates that the cellular tissue growth pathways 34 may extend radially inward to a central region 30. It can be appreciated, therefore, that the cellular tissue growth pathways 34 may be constructed such that they form generally elongated, continuous growth pathways 34 from the outer edge region 32 to the central region 30. During the cellular growth and replication process, endothelial cells can elongate and align with these continuous growth pathways. Therefore, constructing the occlusive member 14 to include long, generally continuous tissue growth pathways arranged to extend radially inward from the outer edge region 32 to the central region 30 may accelerate endothelial migration and achieve the healing of the left atrial appendage more rapidly than if the growth pathways were not present.

The preferred growth pathways 34 described above may be formed from the material and/or structure which is used to manufacture the occlusive member 14. For example, the preferred growth pathways 34 may be formed from a plurality of filaments that are used to construct the occlusive member 14. The filaments may be woven together to form long, generally continuous tissue growth pathways arranged to extend radially inward from the outer edge region 32 to the central region 30. In other examples, the occlusive member 14 may be formed from a single, monolithic sheet of material (e.g., a monolithic sheet of fabric material). Additionally, it can be appreciated that apertures (e.g., openings, etc.) may be formed in the single sheet of material whereby the preferred growth pathways 34 would include the material positioned between the individual apertures. In yet other examples, it can be appreciated that the cellular growth pathways 34 may be embossed onto a monolithic sheet of material which defines the occlusive member 14 (this feature will be further discussed with respect to FIG. 8 below).

Additionally, it is contemplated that the material used to construct the occlusive member 14 may terminate at a central member 36 positioned in the central region 30 of the occlusive member. In some examples, the central member 36 may include a disk or ring structure. The central member 36 may further include a termination surface which is designed to attach to the occlusive member 14. For example, the central member 36 may be attached to one or more filaments which define a particular preferred growth pathway 34. In other examples, the central region may not include a central member.

Figure 5A:
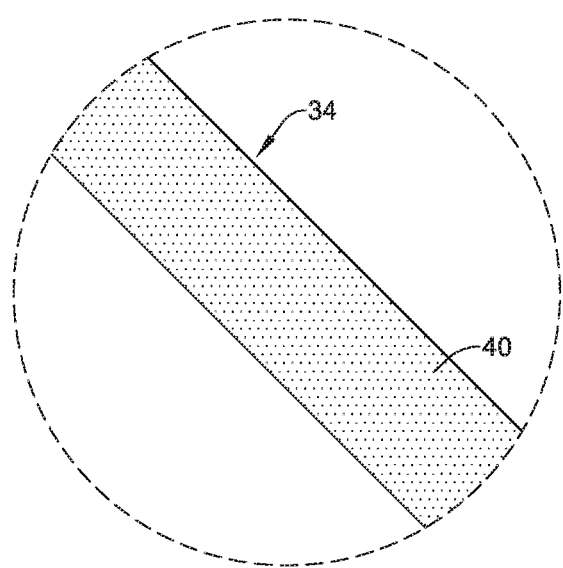
FIG. 5A illustrates a portion of another example occlusive implant.

FIG. 5A illustrates a detailed view of an example cellular growth pathway 34 of the occlusive member 14 discussed above. As shown in FIG. 5A, the cellular growth or migration pathway 34 may include an elongated, continuous filament 40. The filament 40 may be constructed from one or more fibers. For example, the filament 40 may be constructed from a single fiber. However, in other examples the filament 40 may be constructed from a plurality of fibers coupled (e.g., braided, woven, etc.) together. For example, the filament 40 may be constructed from 1, 2, 3, 4, 5, 10, 25, 50 or more fibers.

Alternatively, filament 40 may be constructed from a sheet-like material. For example, filament 40 may be constructed from a fabric sheet of material. It can be appreciated that the filament 40 include a generally straight, long and continuous surface on which cellular tissue (e.g., endothelial tissue) may grow via recruitment and migration. For example, as the endothelial cells grow and replicate along the surface of the growth pathway 34, the endothelial cells may migrate and recruit cells at the leading edge of tissue growth in an effort to fully cover the surface of the growth pathway 34 with a monolayer of endothelium. It can be further appreciated that this generally straight, long and continuous surface may minimize obstructions which may impede the growth of the cellular tissue along its length thereof.

Figure 5B:
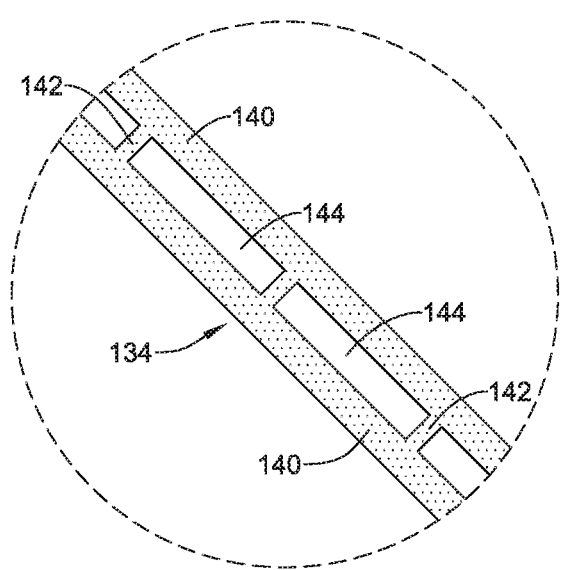
FIG. 5B illustrates a portion of another example occlusive implant.

FIG. 5B illustrates another detailed view of example cellular growth pathway 134 of the occlusive member 14 discussed above. As shown in FIG. 5B, the cellular growth pathway 134 may include a plurality of elongated, continuous filaments 140 positioned adjacent to one another. The filaments 140 may be constructed from one or more fibers. For example, the filaments 140 may be constructed from a single fiber. However, in other examples the filaments 140 may be constructed from a plurality of fibers coupled (e.g., braided, woven, etc.) together. For example, the filaments 140 may be constructed from 1, 2, 3, 4, 5, 10, 25, 50 or more fibers.

Additionally, FIG. 5B illustrates that the filaments 140 may be connected to each other via one or more lateral members 142. It can be appreciated that lateral members 142 are spaced away from each other such that they allow each of the filaments 140 to maintain relatively straight, long and continuous regions between each of the lateral members 142. Further, it can be appreciated that the growth pathway 134 includes a plurality of apertures (e.g., openings) 144 which are bound by the filaments 140 and lateral members 142.

It can be appreciated that each of the filaments 140 and/or the lateral members 142 may be constructed from a single fiber. For example, the filaments 140 and the lateral members 142 may include individual fibers which are woven together to form the general shape (e.g., pattern) of the growth pathway 134 shown in FIG. 5B. Alternatively, the growth pathway 134 (including each of the filaments 140 and lateral members 142) may be constructed from a sheet-like material. For example, the filaments 140 and lateral members 142 may be constructed from a fabric sheet of material. It can be appreciated from FIG. 5B that the filaments 140 may include generally straight, long and continuous surfaces on which cellular tissue (e.g., endothelial tissue) may grow. It can be further appreciated that the lateral members 142 are relatively short members (compared to the filaments 140) and, therefore, will not impede the growth of the cellular tissue along the generally straight, long and continuous surfaces of the filaments 140.

Figure 5C:
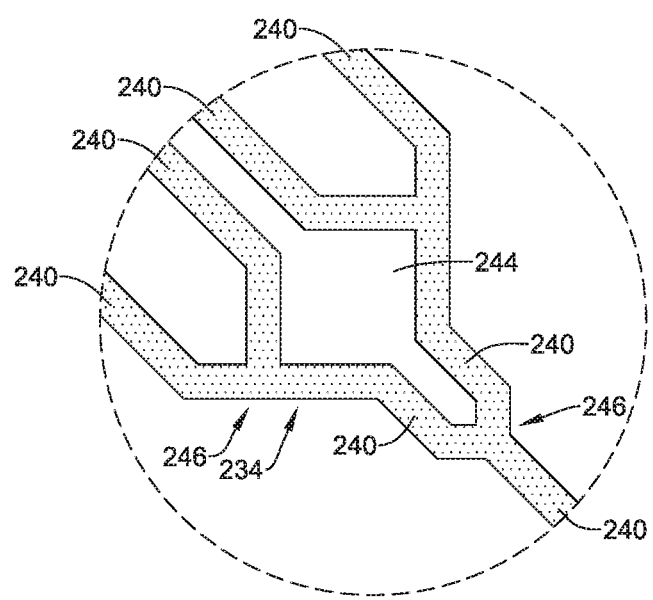
FIG. 5C illustrates a portion of another example occlusive implant.

FIG. 5C illustrates another detailed view of an example cellular growth pathway 234 of the occlusive member 14 discussed above. As shown in FIG. 5A, the cellular growth pathway 234 may include one or more elongated, continuous filaments 240 which are arranged in a "branching" formation. For example, FIG. 5C illustrates that one or more filaments 240 may merge at a convergence point 246. FIG. 5C illustrates multiple convergence points 246 where multiple filaments 240 merge together. It can be appreciated that this type of arrangement may be desirable for constructing growth pathways that extend from an outer region radially inward to a central region (such as those pathways illustrated with respect to the occlusive member 14 described in FIG. 4 above). In other words, it may be desirable to include multiple filaments 240 along an outer circumference of an example occlusive members, whereby the filaments merge and decrease in number as they extend closer to a central region.

Similarly to those described above, the filaments 240 may be constructed from single fibers. For example, the filaments 240 may include individual fibers which are woven together to form the general shape (e.g., pattern) of the growth pathway 234 shown in FIG. 5B. Alternatively, the growth pathway 234 (including each of the filaments 240) may be constructed from a sheet-like material. For example, the filaments 240 may be constructed from a sheet of material (e.g., a fabric sheet). It can be appreciated from FIG. 5B that the filaments 240 may include generally straight, long and continuous surfaces on which cellular tissue (e.g., endothelial tissue) may grow. It can be further appreciated that these generally straight, long and continuous surfaces do not include obstructions which would impede the growth of the cellular tissue along its length thereof. For example, the merge points 246 may improve the efficiency in which the cellular tissue may grow along the pathway 234. Further, it can be appreciated that the growth pathway 234 includes a plurality of apertures (e.g., openings) 244 which are bound by the filaments 240.

Figure 5D:
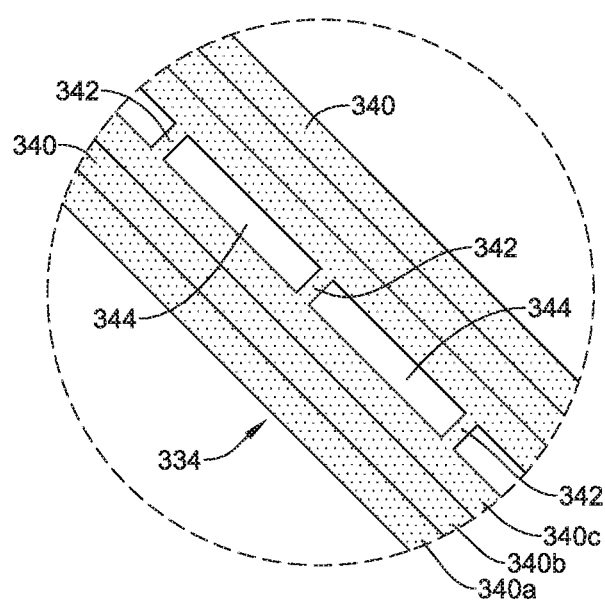
FIG. 5D illustrates a portion of another example occlusive implant.

FIG. 5D illustrates another detailed view of example cellular growth pathway 334 of the occlusive member 14 discussed above. As shown in FIG. 5D, the cellular growth pathway 334 may include a plurality of filament "groups" 340 positioned adjacent to one another. For example, FIG. 5D illustrates that each filament group 340 may include one or more individual filaments 340a/340b/340c. While FIG. 5D shows each filament group 340 including three individual filaments 340a/340b/340c, it is contemplated that each filament group 340 may include more or less than three filaments. For example, each group of filaments may include 1, 2, 3, 4, 5, 6, 7, 8 or more filaments. Further, FIG. 5D illustrates two filament groups 340 arranged adjacent to one another. Additionally, FIG. 5D illustrates that the filament groups 340 may be connected to each other via one or more lateral members 342. It can be appreciated that lateral members 342 may be spaced away from each other such that they allow each of the filament groups 340 to maintain relatively straight, long and continuous regions between each of the lateral members 342. Further, it can be appreciated that the growth pathway 334 includes a plurality of apertures (e.g., openings) 344 which are bound by the filament groups 340 and lateral members 342.

As discussed above, it can be appreciated that each of the filament groups 340 and/or the lateral members 342 may be constructed from individual fibers. For example, the filament groups 340 and the lateral members 342 may include individual fibers which are woven together to form the general shape (e.g., pattern) of the growth pathway 334 shown in FIG. 5D. Alternatively, the growth pathway 334 (including each of the filaments 340a/340b/340c and lateral members 342) may be constructed from a sheet-like material. For example, the filament groups 340 and lateral members 342 may be constructed from a sheet of material (e.g., a fabric sheet). It can be appreciated from FIG. 5D that the filament groups 340 may include generally straight, long and continuous surfaces on which cellular tissue (e.g., endothelial tissue) may grow. It can be further appreciated that the lateral members 342 are relatively short members (compared to the filament groups 340) and, therefore, will not impede the growth of the cellular tissue along the generally straight, long and continuous surfaces of the filament groups 340.

Figure 6:
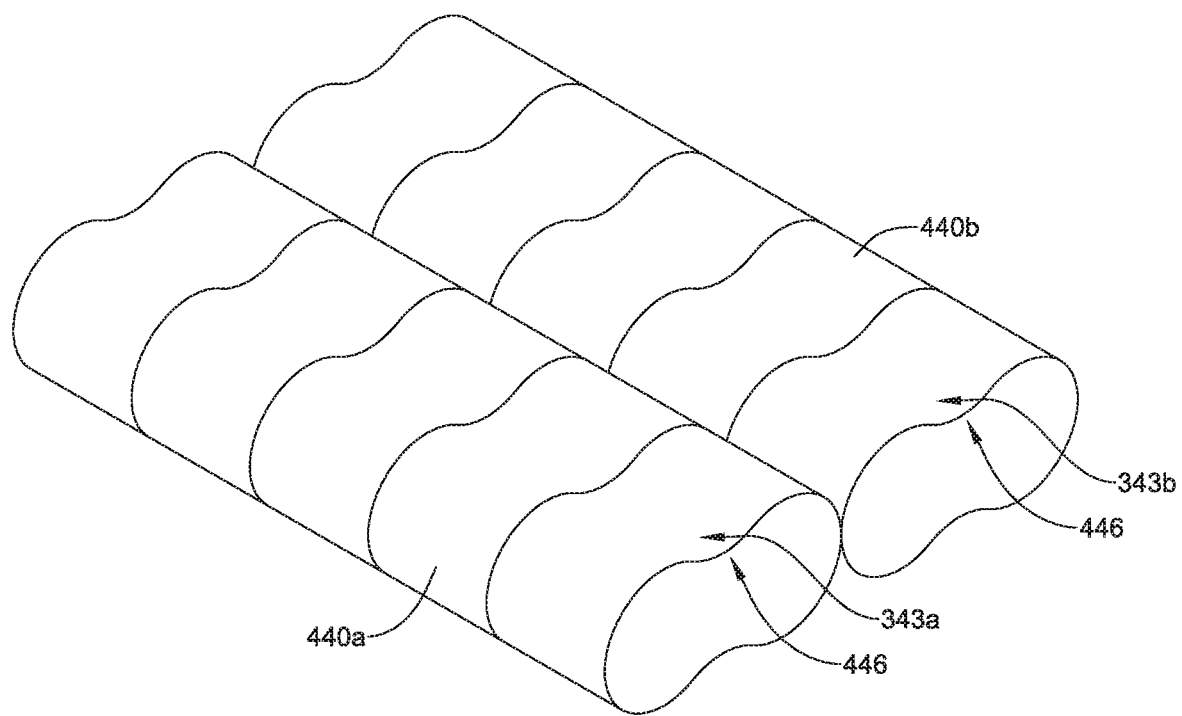
FIG. 6 illustrates a portion of another example occlusive implant.

FIG. 6 illustrates additional example filaments 440a and 440b utilized to form an example occlusive member. As illustrated in FIG. 6, each of the filaments 440a and 440b may include a general "dog-bone" cross-sectional shape, including one or more curved portions 446. It can be appreciated that the curved portions may extend along the entire length of each of the filaments 440a and 440b, thereby forming a longitudinally, continuously extending channels 343a/343b (e.g., groove, etc.) In some examples, an individual the channels 343a/343b may be referred to as a "raceways." It can be appreciated that the channels 343a/343b may encourage cellular tissue to grow along the surface thereof, as the channels 343a/343b include longitudinally extending portions which may "funnel" the tissue to grow along their length and not in directions which are perpendicular to the channels 343a/343b. Additionally, FIG. 6 illustrates that each of the filaments 440a and 440b may be positioned adjacent to one another (and may be attached via lateral members as described above).

Figure 7:
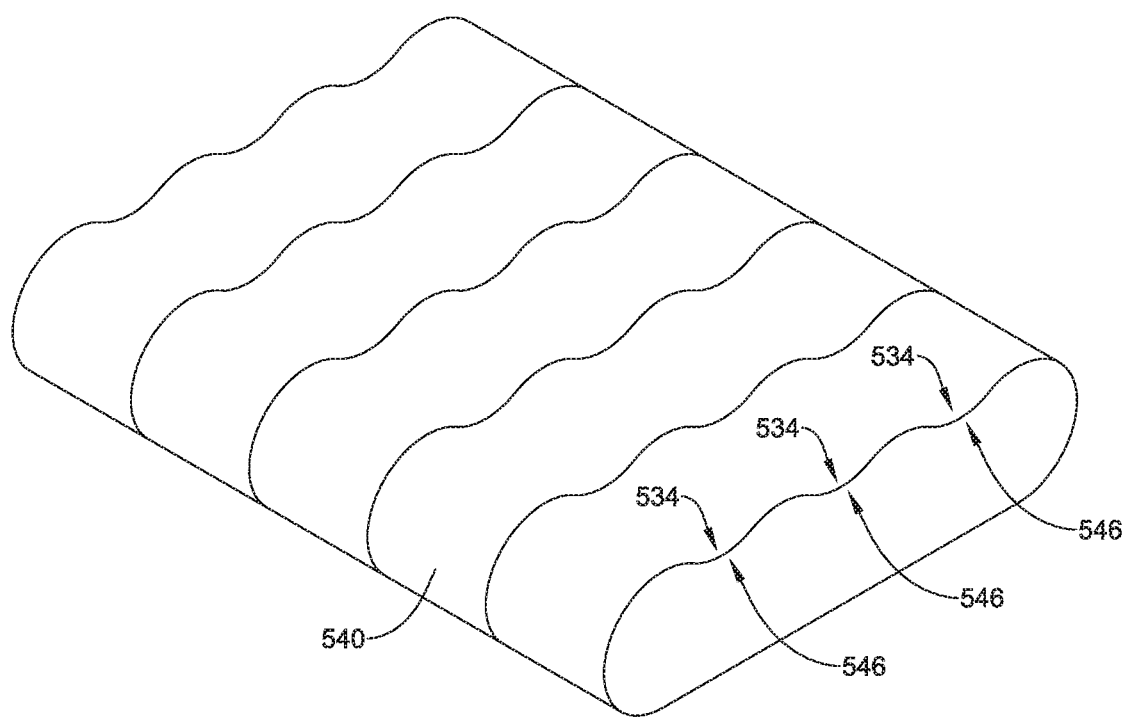
FIG. 7 illustrates a portion of another example occlusive implant.

FIG. 7 illustrates another example filament 540 which may be utilized to form an example occlusive member. As illustrated in FIG. 7, the filament 540 may include a plurality of curved portions 546 which form a plurality of channels 534 extending along the length of the filament 540. In some examples, the individual the channels 534 may be referred to as a "raceways." Like those described above, it can be appreciated that the channels 534 may encourage cellular tissue to grow along the surface thereof, as the channels 534 may include longitudinally extending portions which may "funnel" the tissue to grow along their length and not in directions which are perpendicular to the channels 534.

While FIG. 6 and FIG. 7 illustrate two example filaments including raceways extending along their lengths, other example occlusive members may include filaments having different cross-sectional shapes. Additionally, it can be appreciated that in some examples, the filament designs shown in FIG. 6 and FIG. 7 may be constructed from material sheets (e.g., a fabric sheet) as described above. Further, it can be appreciated that the cross-sectional shapes shown in FIG. 6 and FIG. 7 may vary in their specific shape (including the number curves, etc.), but may all serve a similar purpose in encouraging cellular tissue to grow along their length while discouraging the tissue from growing in directions which would impede their longitudinal growth. Further, it is contemplated that the filaments described in FIG. 6 and FIG. 7 may be utilized in any of the occlusive device examples described herein.

Figure 8:
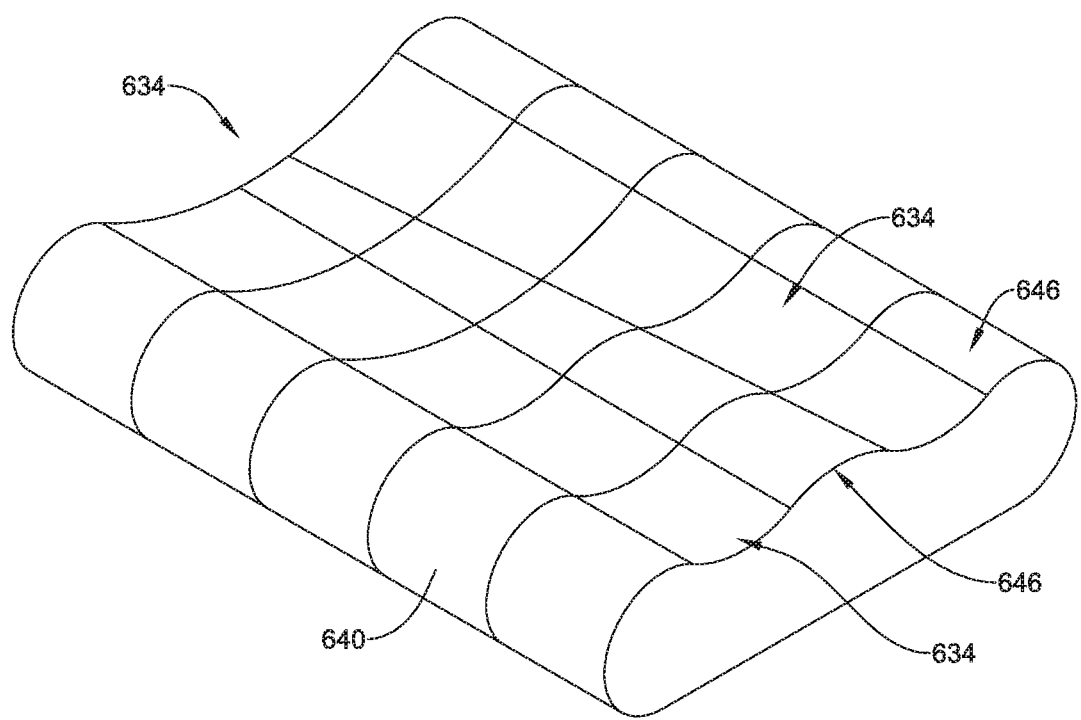
FIG. 8 illustrates a portion of another example occlusive implant.

It is further contemplated that any of the patterns, designs and/or arrangements of the growth pathways (including the raceways described above) or combinations thereof may be constructed by embossing, etching, etc. the features onto a sheet of material (e.g., a fabric sheet, a metallic sheet, etc.). It can be appreciated that these processing techniques (e.g., embossing, etching, etc.) may create growth pathways which extend radially outward and may minimize obstructions to cellular growth. For example, FIG. 8 illustrates an example structure 640 which may be utilized to form an example occlusive member. The structure 640 may include a filament or a sheet of material, for example. Further, as illustrated in FIG. 8, the structure 640 may include a plurality of raised portions 646 which form a plurality of channels 634 extending along the structure 640. As described above, it can be appreciated that the channels 634 may encourage cellular tissue to grow along the surface thereof, as the channels 634 may "funnel" the tissue to grow along their length and minimize growth in directions which are perpendicular to the channels 634. Additionally, FIG. 8 illustrates that two or more channels 634 may merge together without creating an obstruction to endothelial tissue growth. The raised portions 646 and the channels 634 may be formed via an embossing or etching process as described above.

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein) to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:
1. An occlusive implant, comprising:
an expandable framework configured to shift between a collapsed configuration and an expanded configuration; and
an occlusive member disposed along at least a portion of the expandable framework;

wherein the occlusive member includes a plurality of elongated, straight, continuous filaments that form a plurality of discrete elongated, straight, continuous cellular tissue growth pathways, wherein the pathways extend radially away from a central region of the occlusive member, wherein the central region of the occlusive member includes a termination member, wherein at least one of the filaments forming a first cellular growth pathway is coupled to the termination member, wherein the first cellular growth pathway is continuous between the termination member and an outer edge region of the implant, wherein at least one of the plurality of elongated, straight, continuous filaments includes a longitudinally extending channel, and wherein the channel is configured to promote cellular tissue growth along its length thereof.

2. The occlusive implant of claim 1, wherein the plurality of elongated, straight, continuous filaments are woven together.

3. The occlusive implant of claim 1, wherein the occlusive member includes a monolithic sheet of material.

4. The occlusive implant of claim 3, wherein the monolithic sheet of material has one or more apertures therein, and wherein the pathways are formed from material extending between the one or more apertures.

5. The occlusive implant of claim 1, wherein at least two of the plurality of elongated, straight, continuous filaments are coupled together via at least one lateral member.

6. The occlusive implant of claim 1, wherein the occlusive implant further comprising a second tissue growth pathway positioned adjacent to the first elongated, straight, continuous cellular tissue growth pathway.

7. A medical implant for occluding a left atrial appendage, comprising:
an expandable framework configured to shift between a collapsed configuration and an expanded configuration; and
an occlusive member disposed along at least a portion of the expandable framework, the occlusive member including a central region;
wherein the occlusive member includes a plurality of elongated, straight, continuous filaments that form a plurality of discrete elongated, straight, continuous cellular growth pathways extending radially away from the central region;
wherein each of the cellular growth pathways is configured to promote continuous cellular tissue growth along its length thereof,
wherein at least one of the plurality of elongated, straight, continuous filaments includes a longitudinally extending channel, and wherein the channel is configured to promote cellular tissue growth along its length thereof.

8. The occlusive implant of claim 7, wherein the plurality of elongated, straight, continuous filaments are woven together.

9. The occlusive implant of claim 7, wherein the occlusive member includes a monolithic sheet of material.

10. The occlusive implant of claim 9, wherein the monolithic sheet of material has one or more apertures therein, and wherein the plurality of cellular growth pathways are formed from material extending between the one or more apertures.

11. The occlusive implant of claim 7, wherein at least two of the plurality of elongated, straight, continuous filaments are coupled together via at least one lateral member.

12. A method for occluding a left atrial appendage, the method comprising:
advancing an occlusive implant to the left atrial appendage, the occlusive implant including:
an expandable framework; and
an occlusive member disposed along at least a portion of the expandable framework,
wherein the occlusive member includes a central region;
wherein the occlusive member includes a plurality of elongated, straight, continuous filaments that form a plurality of discrete elongated, straight, continuous cellular tissue growth pathways coupled to a termination member and extending radially away from the central region; wherein at least one of the plurality of elongated, straight, continuous filaments includes a longitudinally extending channel, and wherein the channel is configured to promote cellular tissue growth along its length thereof, and
expanding the expandable framework within the left atrial appendage.

* * * * *